US006971617B2

(12) United States Patent
Nguyen

(10) Patent No.: US 6,971,617 B2
(45) Date of Patent: Dec. 6, 2005

(54) APPARATUS FOR SUPPORTING MEDICAL FLUIDS

(75) Inventor: Van Nguyen, South Houston, TX (US)

(73) Assignee: Texas Children's Hospital, Houston, TX (US)

( * ) Notice: Subject to any disclaimer, the term of this patent is extended or adjusted under 35 U.S.C. 154(b) by 378 days.

(21) Appl. No.: 09/849,907

(22) Filed: May 4, 2001

(65) Prior Publication Data
US 2002/0162926 A1 Nov. 7, 2002

(51) Int. Cl.$^7$ .............................................. E04G 3/00
(52) U.S. Cl. .......................... 248/286.1; 248/229.15; 211/172; 403/97; 403/381
(58) Field of Search .................... 248/229.15, 161, 248/125.1, 227.4, 311.3, 286.1, 287.1, 318, 248/102, 103, 316.1, 316.4, 228.3; 5/503.1, 5/282.1, 658; 403/104, 191, 261, 373, 381, 403/83–85, 97–98, 93; D24/128; 211/85.13, 211/113, 60.1, 94.01, 162, 99, 100, 171, 172

(56) References Cited

U.S. PATENT DOCUMENTS

| | | | | |
|---|---|---|---|---|
| 837,642 | A | * 12/1906 | Powell | ........................ 248/95 |
| 1,865,757 | A | * 7/1932 | Honsowetz | .................. 211/172 |
| 2,957,187 | A | * 10/1960 | Raia | ............................ 5/503.1 |
| 3,709,372 | A | * 1/1973 | Alexander | .................... 211/74 |
| 3,709,556 | A | * 1/1973 | Allard et al. | ................ 297/188 |
| 4,042,232 | A | * 8/1977 | Lile et al. | .................... 269/328 |
| 4,332,378 | A | 6/1982 | Pryor | |
| 4,511,157 | A | 4/1985 | Wilt, Jr. | |
| 4,547,092 | A | * 10/1985 | Vetter et al. | ................... 403/59 |
| 4,725,027 | A | 2/1988 | Bekanich | |
| 4,744,536 | A | 5/1988 | Bancalari | |
| 4,832,294 | A | 5/1989 | Eidem | |
| 4,875,651 | A | * 10/1989 | Wergin et al. | ............... 248/286 |
| 4,905,944 | A | 3/1990 | Jost et al. | |
| 5,110,076 | A | 5/1992 | Snyder et al. | |
| 5,407,163 | A | * 4/1995 | Kramer et al. | .............. 248/291 |
| 5,499,721 | A | * 3/1996 | Hansen et al. | ................. 211/13 |
| 6,231,016 | B1 | * 5/2001 | Slone | ....................... 248/200.1 |

\* cited by examiner

*Primary Examiner*—Gwendolyn Baxter
(74) *Attorney, Agent, or Firm*—Howrey LLP

(57) ABSTRACT

An apparatus for supporting medical fluids for delivery to a patient during surgery, in particular for fluids for intravenous delivery to the patient, is provided. The apparatus comprises a clamp for removably securing the apparatus to an object, such as a surgical table or bed, to allow the object to support the apparatus, the object being immovable relative to the patient to which the fluids are to be delivered. An arm is provided extending from the clamp. A support is connected to the arm remote from the clamp, the support being adapted to retain a receptacle containing medical fluids. In one embodiment, the arm is movable longitudinally with respect to the clamp, thereby allowing the position of the support with respect to the clamp to be adjusted. In a second embodiment, the arm is rotatable about the clamp such that the fluid receptacle support may be moved within a plane containing the longitudinal axis of the arm.

20 Claims, 3 Drawing Sheets

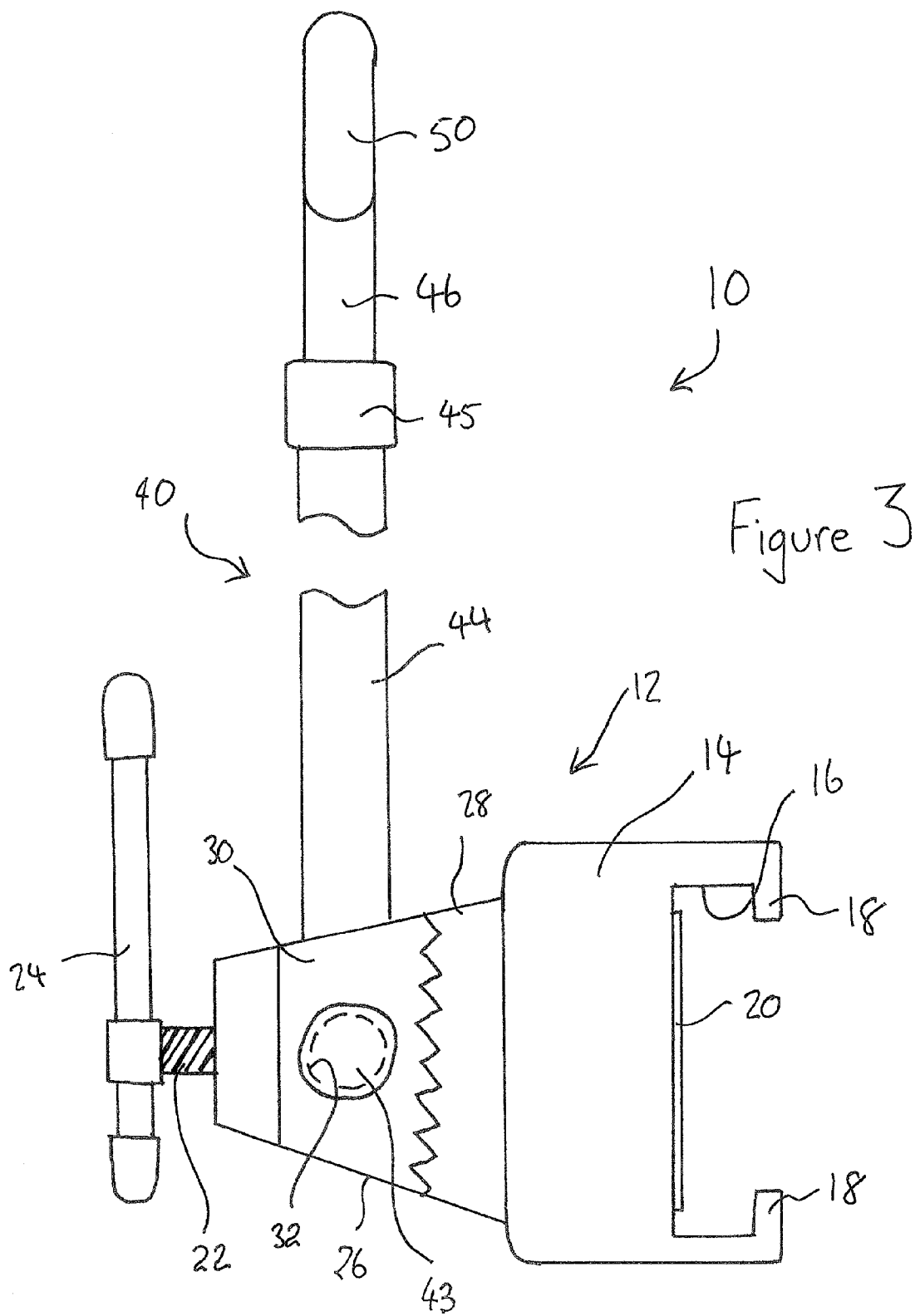

APPARATUS FOR SUPPORTING MEDICAL FLUIDS

The present invention relates to an apparatus for supporting medical fluids for delivery to a patient, in particular medical fluids for delivery to a patient intravenously. The present invention especially relates to an apparatus for use in an operating room for supporting medical fluids for intravenous delivery to a patient during a surgical procedure.

BACKGROUND OF THE INVENTION

Many aspects of patient treatment and care require that medical fluids, such as blood, blood plasma and saline solutions, be administered to the patient intravenously. It is also common practice for certain drugs to be administered in this manner. One area of widespread use of intravenously administered fluids is during surgery. The majority of surgical procedures require patients to receive fluids intravenously, prolonged surgery requiring often high volumes of fluids to be delivered in this manner. Accordingly, receptacles of medical fluids and the equipment for intravenous delivery of the fluids to the patient are common features in any operating room Commonly, fluids for intravenous delivery are contained in bags or bottles, suspended from supports. During the surgical procedures, the bags or bottles containing the fluids are connected to the patient by lines through which the fluid flows. Flow may be induced by gravity. Alternatively, the flow may be induced and controlled by the use of an infusion device or pump. Support apparatus for use in supporting the fluid containers are well known in the art and typically comprise a base, from which a pole or rod extends vertically upwards. The pole or rod is typically of a telescopic construction, allowing the height of the support device to be adjusted. One or more hooks are typically connected to the upper end of the pole or rod, from which the fluid containers are suspended, when in use. The base is supported on wheels or casters, allowing the entire apparatus to be mobile and moved. Examples of such support devices are disclosed in U.S. Pat. Nos. 4,332,378, 4,744,536, 4,832,294, 4,905,944 and 5,110,076. The support devices disclosed, while generally applicable to the provision of intravenous fluids to a patient, are intended to be used is situations in which the mobility of the patient, for example when moving about a hospital or when being treated at home, is not to be hindered.

In addition to their intended applications in providing intravenous fluids while maintaining patient mobility, support devices of the aforementioned type are also employed within an operating room during surgical procedures. However, such devices present a number of serious disadvantages when employed in the surgical environment. In general, surgical procedures require the surgeon and attendant support staff, such as anesthesiologists and surgical nurses, to be able to move freely around the patient and have unimpaired access to the patient. As the complexity of the surgical procedures increases, the number of persons in attendance during the operation increases, in turn increasing the problem of access to the patient. In addition, as the complexity of the surgical procedures increases, the amount of ancillary equipment employed increases, in turn reducing the room available around the patient for the surgeon and support staff to maneuver and access the patient. An example of such a complex surgical procedure in which these problems are very evident is cardio-vascular operations, for example open heart surgery. Within this environment, the traditional support device for delivering intravenous fluids represents a major obstacle to the freedom of mobility of the surgical staff around the patient, often interfering with surgical procedures and acting as a distraction.

A further problem also arises with the aforementioned support devices during surgical procedures. During many surgical procedures, the blood pressure of the patient is monitored using a transducer. The transducer is mounted so as to be on the same horizontal level as the mid atrial line of the patient. It is common practice to secure the transducer to the mid to lower portion of the intravenous fluid support device at the appropriate height. However, during the course of the operation, it can occur that the support device is moved and its height adjusted. This in turn alters the level of the transducer, rendering its readout inaccurate.

Despite the aforementioned problems attendant with the use of the conventional intravenous fluid support apparatus, these devices remain in widespread use in operating rooms and surgeries throughout hospitals and clinics. Clearly, an improved design of support apparatus is required.

U.S. Pat. No. 4,511,157 discloses an apparatus for connecting a portable, wheeled stand for intravenous fluids to a wheelchair. The apparatus comprises a support arm extending from the stand to engage with a suitable support member attached to the wheelchair. The object of the apparatus is to allow the stand to be connected to the wheelchair in such a manner as to allow a person pushing the wheelchair to push and raise the wheelchair during normal use, without being hindered by the attached stand. It will be appreciated that the apparatus is intended to allow the patient seated in the wheelchair to retain full mobility. Accordingly, this apparatus does not solve any of the problems arising from the known support stands, when used in an operating room or other surgical environment.

U.S. Pat. No. 4,725,027 discloses an intravenous equipment support. The support is intended to be used in conjunction with a wheelchair or other means of patient is transport, for example a stretcher. The support generally comprises a telescopic pole, which may be free-standing, in which case it is provided with its own wheeled base, or may be fixed to a wheelchair or other similar device. A hook or similar device is provided on the upper end of the pole for supporting one or more containers of intravenous fluid. In one embodiment, the support comprises the telescopic pole, which is mounted onto a stretcher. With this embodiment, with the exception of being height-adjustable, the orientation of the fluid containers remains fixed with respect to the stretcher.

The device of U.S. Pat. No. 4,725,027 is clearly intended to be employed in a situation in which the patient is to remain mobile. During surgical procedures, the patient is not required to be mobile. Rather, the patient is generally restrained in one position throughout the procedure. Accordingly, the device of U.S. Pat. No. 4,725,027 does not meet all the needs of a support device for use in a surgical operating room.

U.S. Pat. No. 3,709,556 discloses a holder for containers for intravenous fluids for attachment to portable patient conveyances. The holder may be used in two embodiments. In the first, the holder comprises a vertical rod, which may be attached to the rear of a wheelchair, adjacent one of the handles used by an attendant to push the chair. In the second embodiment, the holder again comprises a vertical rod, for attachment to a wheeled stretcher or gurney. The rod is attached to one leg of the gurney by means of two horizontal arms, each terminating in a clamp extending around the leg. The clamps, while not easily removed from the leg, may be released to allow the rod to swing in an arc about the leg.

Again, the apparatus of U.S. Pat. No. 3,709,556 is intended to facilitate patient mobility, while allowing the patient to receive fluids intravenously. For this reason alone, the apparatus is not intended for use in a surgical environment and does not address or solve the problems attendant with delivering intravenous fluids to a patient while surgery is underway. In particular, the apparatus of U.S. Pat. No. 3,709,556 does not allow a wide range of movement of the support rod, this being limited to an arcuate movement about one leg of the gurney.

Accordingly, there remains a need for an improved apparatus for supporting fluids for delivering to a patient during surgery in an operating room or the like.

SUMMARY OF THE INVENTION

The present invention provides an apparatus for supporting fluids for delivery to a patient. The apparatus is particularly suitable for use during surgical procedures in an operating room or similar locations.

According to a first aspect of the present invention, there is provided an apparatus for supporting medical fluids for delivery to a patient during surgery, the device comprising:

a clamp for removably securing the device to an object to allow the object to support the apparatus, the object being immovable relative to the patient to which the fluids are to be delivered;

an arm extending from the clamp;

a support connected to the arm remote from the clamp, the support being adapted to retain a receptacle containing medical fluids;

the arm being movable longitudinally with respect to the clamp, thereby allowing the position of the support with respect to the clamp to be adjusted.

The apparatus is particularly suited for use in an operating room or other environment where surgical operations take place. The apparatus is most conveniently secured by means of the clamp to an item of surgical furniture upon which the patient is intended to lie, in particular a table or bed.

In a second aspect, the present invention provides an apparatus for supporting receptacles for medical fluids for intravenous delivery to a patient, the support device comprising:

a clamp for releasably securing the device to an item of surgical furniture;

a first arm extending from the clamp;

a second arm extending from the first arm; and a fluid receptacle support mounted on the second arm;

wherein the first arm and second arm are movable with respect to the clamp such that the fluid receptacle support may be moved within a plane containing the longitudinal axis of the first arm and the longitudinal axis of the second arm.

The arm extending from the clamp does so laterally from the clamp, while allowing the apparatus when secured to an object, such as a surgical table, to occupy a minimum of space. The apparatus of the present invention is particularly advantageous in that it allows the necessary receptacles or containers of fluid to be administered to a patient, for example intravenously, to be supported close to the patient, while presenting the minimum of obstacles to the persons in attendance during the surgery and performing the surgical procedures. The apparatus is particularly adaptable to a variety of situations in the operating room, by reason of the releasable clamp allowing the apparatus to be placed in the most convenient location with respect to the patient and adjusted to allow the receptacles of fluid to be supported in the most appropriate position.

BRIEF DESCRIPTION OF THE DRAWINGS

The present invention will be understood more fully from the detailed description given herein below and from the accompanying drawings of preferred embodiments of the invention. The description and drawings should not be taken to limit the invention to the specific embodiments, but are for explanation and understanding purposes only.

In the drawings:

FIG. 3 is an end elevation along the line A—A of the embodiment of the apparatus shown in FIG. 2.

DESCRIPTION OF ILLUSTRATIVE EMBODIMENTS

Figure 1:
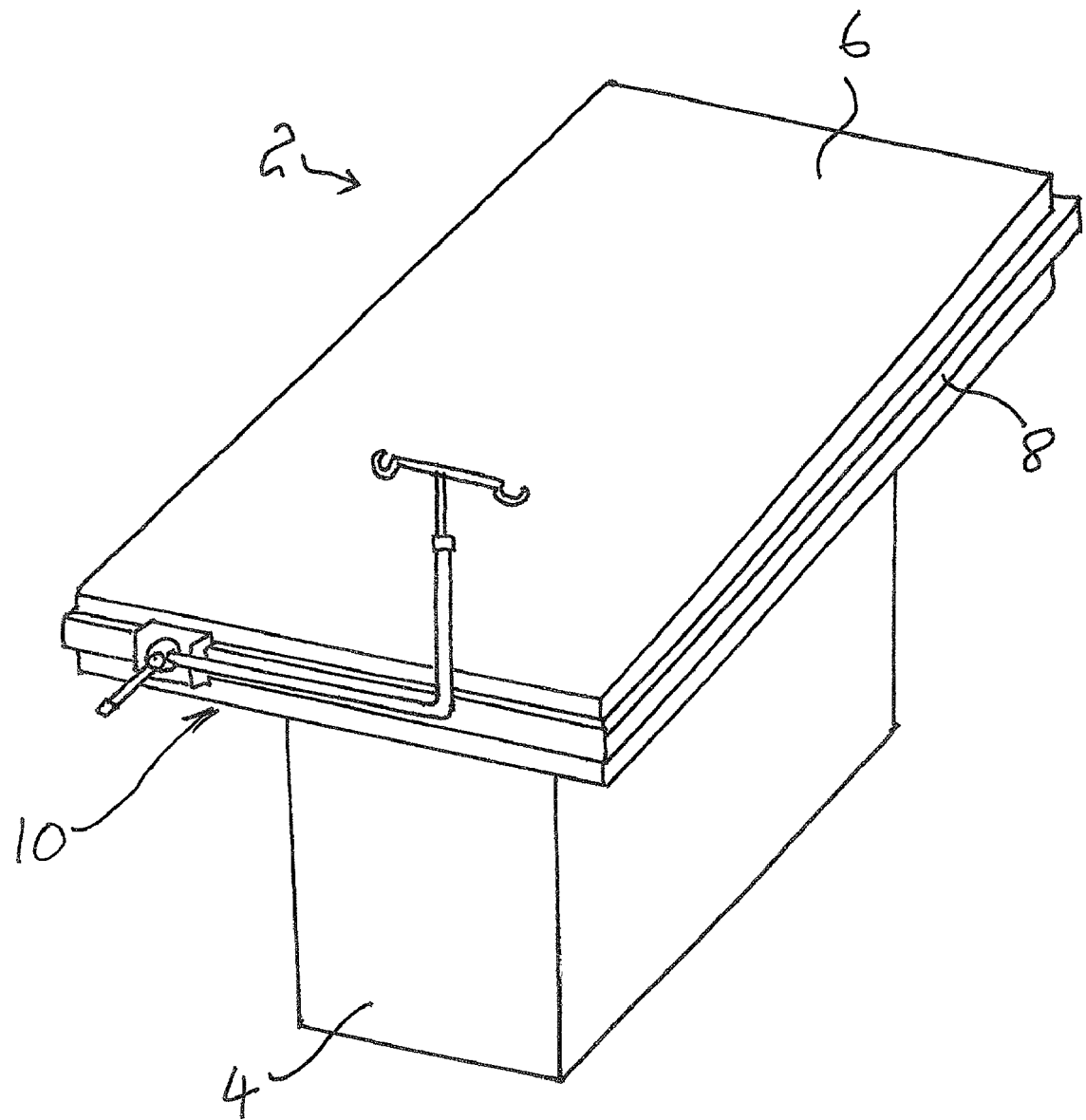
FIG. 1 is a perspective representation of one embodiment of the apparatus of the present invention in place on a surgical table.

Referring to FIG. 1, a surgical table of conventional, known design is shown and generally indicated as 2. The surgical table 2 comprises a base 4, upon which is supported a table top 6. The table top is provided with a lateral rail 8, extending along each side of the table top. One embodiment of the apparatus of the present invention, generally indicated as 10, is shown secured to the lateral rail 8 at one end of the table top 6. In use during a surgical operation, the apparatus 10 is typically under the supervision of an anesthetist in attendance throughout the surgical procedures. Typically, the anesthetist is positioned at the head of the patient, in which case, the apparatus 10 is conveniently attached to the rail 8 at that end of the table top 6. It will however be understood that it is an advantage of the apparatus of the present invention that it may be easily secured to the table top at any convenient location, or indeed to another item of equipment present in the operating room that provides a convenient and practical location from which to dispense medical fluids to be administered to the patient and that is immovable relative to the patient during the surgical procedures.

Figure 2:
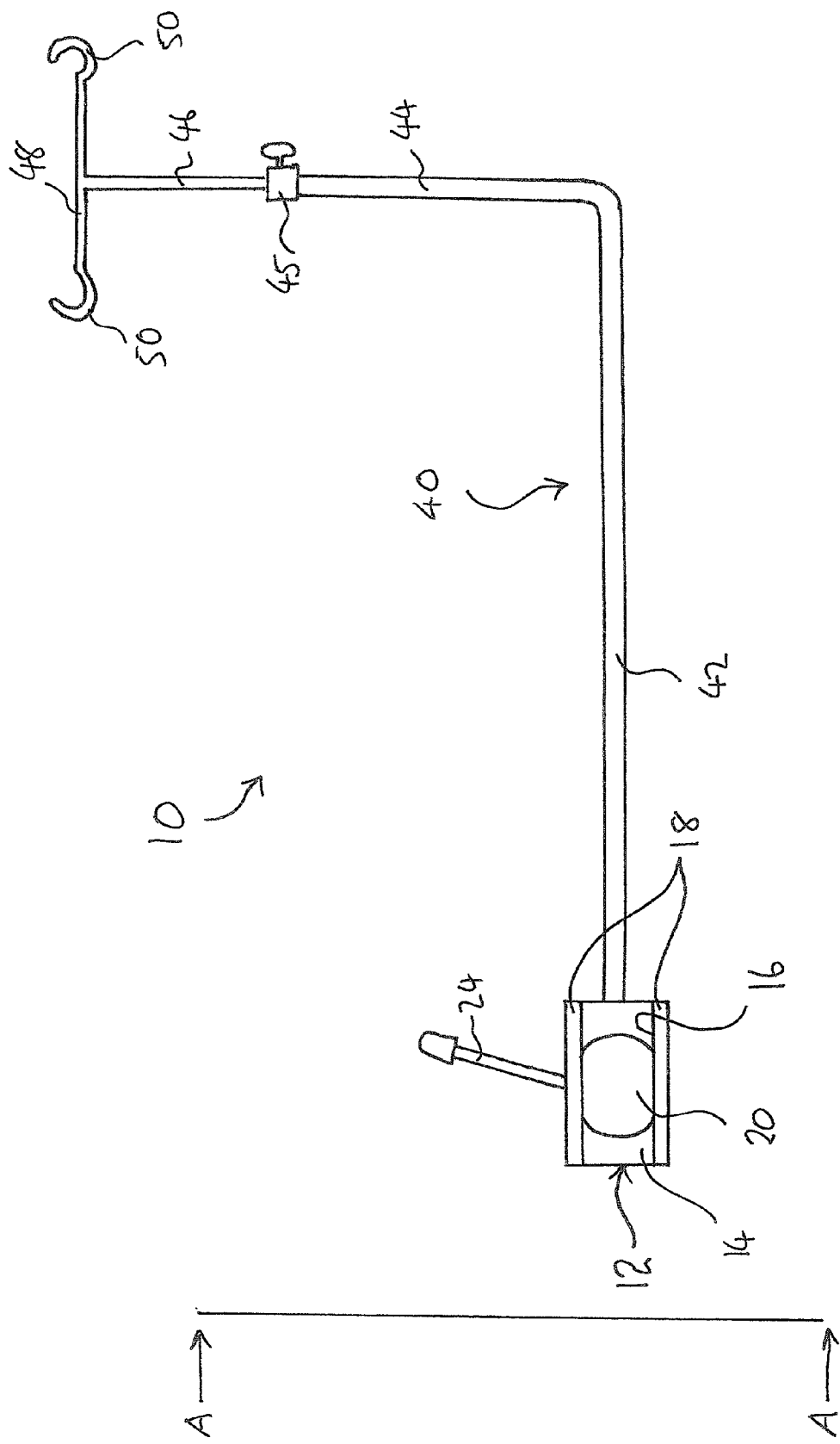
FIG. 2 is a side elevation of the embodiment of the apparatus shown in FIG. 1.

The apparatus 10 of FIG. 1 is shown in side elevation in FIG. 2 and in end elevation in FIG. 3. Referring to FIGS. 2 and 3, the apparatus 10 comprises a clamp 12 adapted to secure the apparatus to the rail 8 extending along the edge of the table top 6 (as shown in FIG. 1). The clamp 12 may be adapted to secure the apparatus to other items of equipment present in the operating room, as mentioned above. Clamps suitable for use as the clamp 12 are known in the art and are available commercially. One preferred form of clamp for use as the clamp 12 is shown in end elevation in FIG. 2 and comprises a clamp body 14 having on one major face a groove 16 defined by lips 18. The groove 16 accepts the rail 8 of the surgical table 2, with the lips 18 retaining the clamp body 14 slidably engaged with the rail 8. A circular clamping member 20 is retained in the clamp body 14, from which it is extendable by the action of a threaded rod 22 extending through the clamp body 14 and being rotated by a handle 24. The clamping member 20, when extended, acts against the lips 18 to lock the clamp body 14 onto the rail 8.

The clamp further comprises a frusto-conical locking boss 26, having first and second locking portions 28 and 30. The second locking portion 30 is provided with a lateral bore 32 therethrough. The opposing faces of the first and second locking portions 28 and 30 are provided with a toothed contour. The action of tightening the clamp 12 by rotating the threaded rod 22 forces the first and second locking portions 28 and 30 into engagement, thereby preventing relative rotation of one locking portion with the other. When the clamp 12 is loosened, the second locking portion 30 may be moved away from and out of engagement with the first locking portion 28, thereby allowing the second locking portion 30 to rotate with respect to the first locking portion 28 and the clamp body 14.

The apparatus 10 further comprises an arm assembly, generally indicated as 40, comprising a first arm portion 42 and a second arm portion 44 extending from one end of the first arm portion. The second end of the first arm portion 42 is provided with a portion of increased diameter to act as a stop 43. The first arm portion 42 extends through the bore 32 in the second locking portion 30 of the clamp boss 26. When the clamp 12 is loosened, the first arm portion 42 is free to slide longitudinally through the bore 32, with movement being limited by the second arm portion 42 and the stop 43. Locking the clamp 12 acts to lock the first arm portion 42 in place in the clamp boss 26.

The second arm portion 44 extends from one end of the first arm portion 42 and is perpendicular to the longitudinal axis of the first arm portion 42. In normal use of the apparatus 10, the arm assembly 40 is oriented such that the first arm portion 42 extends substantially horizontally from the clamp 12, with the second arm portion 44 extending substantially vertically, as shown in FIG. 1. It will be appreciated that the orientation of the arm assembly 40 may be moved within a plane about the clamp 12, by virtue of the second locking portion 30 being rotatable with respect to the first locking portion 28. In this way, the arm assembly 40 may be maintained with the first arm portion 42 substantially horizontal, while the table 2 is tilted, as may be required during some surgical procedures. Further, the first arm portion 42, and hence the entire arm assembly 40, is free to rotate with respect to the clamp 12 about the longitudinal axis of the first arm portion 42, when the clamp 12 is loosened. In this way, the arm assembly may be oriented to extend from either side of the clamp 12, as required by the positioning of the clamp 12 on the rail 8 along the table 2 and the surgical procedures taking place. This represents a significant versatility in the freedom to position the apparatus 10 in general and the arm assembly 40 in particular.

A support rod 46 is mounted to the end of the second arm portion 44. The support rod 46 is movable with respect to the second arm portion 44. A support rod clamp 45 is used to fasten the support rod 46 in the desired position. As shown in FIGS. 1 to 3, the support rod 46 extends telescopically within the second arm portion 44. However, it will be appreciated that alternative arrangements allowing the position of the support rod 46 to be varied with respect to the second arm portion 44 may also be employed. A hook assembly 48 is attached to an end of the support rod 46 and comprises two hooks 50, from which can be suspended receptacles or containers of medical fluids. Typically, medical fluids are contained in bags, which may be easily hung from the hooks 50.

In FIGS. 1 and 3, the second arm portion 44 is shown as being integral with the first arm portion 42. In an alternative embodiment, the second arm portion 44 may be a separate component, attached to the first arm portion 42 by means of a clamp. In such an embodiment, the second arm portion 44 may be positioned along the first arm portion 42 by releasing the clamp. Such an arrangement would also allow the second arm portion 44 to rotate around the first arm portion 42, allowing the arm assembly 40 to be oriented on the opposite side of the clamp 12, as discussed above.

Provision may be made on the first or second arm portions 42 or 44 for supporting other equipment, for example a transducer assembly for monitoring a patient's blood pressure, as discussed above.

With the apparatus 10 set up and fixed in position in a convenient location, the medical fluids for delivery to the patient, for example intravenously, are secured with no possibility of being disturbed accidentally during the surgical procedures. Further, because of its configuration and the freedom to adjust the orientation of the arm assembly 40, in terms of being one side of the clamp 12 or the other and in terms of the distance of the second arm portion 42 from the clamp 12, the apparatus of the present invention presents a minimum obstacle to surgeons and other persons in attendance during the surgery.

While the particular embodiments for the apparatus of the present invention as herein disclosed in detail are fully capable of obtaining the objects and advantages herein stated, it is to be understood that they are merely illustrative of the presently preferred embodiments of the invention and that no limitations are intended by the details of method of operation, details of construction or design herein shown other than as described in the appended claims.

What is claimed is:

1. An apparatus for supporting medical fluids for delivery to a patient during surgery, the apparatus comprising:
   a clamp for removably securing the apparatus to an object to allow the object to support the apparatus, the object being immovable relative to the patient to whom the fluids are to be delivered;
   an arm having a first longitudinal axis extending from a first end of the clamp;
   a support connected to the arm, the support being adapted to retain a receptacle containing medical fluids;
   the arm being rotatably movable within a plane about the clamp;
   wherein the arm is movable along the first longitudinal axis and rotatably moveable about the first longitudinal axis such that the arm may be oriented to extend from a second end of the clamp, directly opposed to the first end of the clamp, while still supporting medical fluids;
   wherein the arm comprises a first portion extending from the clamp and a second portion extending from the first portion, wherein the first portion of the arm has the first longitudinal axis and the second portion of the arm has a second longitudinal axis and wherein the first longitudinal axis is substantially perpendicular to the second longitudinal axis; and
   wherein the movement of the arm along the first longitudinal axis is limited by the second portion of the arm.

2. An apparatus as claimed in claim 1, wherein the first portion of the arm is rotatable about the clamp within a plane containing the first longitudinal axis of the first portion.

3. An apparatus as claimed in claim 1, wherein the second portion of the arm is rotatable about the first portion of the arm.

4. An apparatus as claimed in claim 1, wherein the first portion of the arm is rotatable about the first longitudinal axis with respect to the clamp.

5. An apparatus as claimed in claim 1, wherein the object is an item of surgical furniture selected from a surgical table and surgical bed, upon which a patient lies.

6. An apparatus as claimed in claim 1, wherein the object is a surgical table, the clamp being adapted to releasably secure to a rail extending along an edge of the surgical table.

7. An apparatus as claimed in claim 1, wherein the support is adapted to retain the receptacle containing medical fluids for delivery to the patient intravenously.

8. An apparatus as claimed in claim 1, wherein the support is mounted on a rod, the rod being mounted to an end of the arm, and wherein the rod is moveable with respect to the end of the arm, and wherein the rod extends telescopically within the arm.

9. An apparatus as claimed in claim 1, wherein the movement of the arm along the first longitudinal axis is limited by an end of the first portion of the arm having an increased diameter.

10. An apparatus as claimed in claim 1, wherein the support retains the receptacle containing medical fluids at a position on the support that is elevated respective to the patient.

11. An apparatus for supporting receptacles containing medical fluids for intravenous delivery to a patient, the apparatus comprising:
 a clamp for releasably securing the apparatus to an item of furniture;
 a first arm portion extending from a first end of the clamp, wherein the first arm portion has a first longitudinal axis;
 a second arm portion extending from the first arm portion, wherein the second arm portion has a second longitudinal axis perpendicular to the first longitudinal axis; and
 a receptacle support mounted on the second arm portion;
 wherein the first arm portion and second arm portion are movable with respect to the clamp such that the receptacle support may be moved within a plane containing the first longitudinal axis and the second longitudinal axis;
 wherein the receptacle support is mounted on a support rod, the support rod being axially mounted to an end of the second arm portion and movable with respect to the end of the second arm portion;
 wherein the first arm portion is movable along the first longitudinal axis, the movement along the first longitudinal axis being limited by an end of the first arm portion having an increased diameter; and
 wherein the movement of the first arm portion along the first longitudinal axis is limited by the second arm portion.

12. An apparatus as claimed in claim 11, wherein the first arm portion is rotatable about the first longitudinal axis with respect to the clamp.

13. An apparatus as claimed in claim 11, wherein the first arm portion is rotatable about the clamp in a plane containing the first longitudinal axis of the first arm portion.

14. An apparatus as claimed in claim 11, wherein the second arm portion is rotatable about the first arm portion.

15. An apparatus as claimed in claim 11, wherein the support rod extends telescopically within the second arm portion.

16. An apparatus as claimed in claim 11, wherein the item of furniture is selected from a surgical table or surgical bed, upon which a patient lies.

17. An apparatus as claimed in claim 11, wherein the item of furniture is a surgical table, the clamp being adapted to releasably secure to a rail extending along an edge of the surgical table.

18. An apparatus as claimed in claim 11, wherein the receptacle support comprises of a hook assembly attached to an end of a support rod, wherein the hook assembly comprises a hook from which receptacles containing medical fluids may be supported and wherein the support rod is axially mounted to the second arm portion and movable with respect to the end of the second arm portion.

19. An apparatus as claimed in claim 18, wherein the hook assembly is elevated from the item of furniture when the support rod is extended.

20. An apparatus of claim 11, wherein the first arm portion is rotatably movable about the clamp and rotatably moveable about the first longitudinal axis such that the first arm portion may be oriented to extend from a second end of the clamp while supporting receptacles containing medical fluids.

* * * * *